United States Patent [19]

Hirao et al.

[11] Patent Number: 4,845,199

[45] Date of Patent: Jul. 4, 1989

[54] PROCESS FOR HEAT TREATING CHEMICALLY UNMODIFIED GAMMA-GLOBULIN

[75] Inventors: Yutaka Hirao, Osaka; Katuhiro Uriyu, Nara; Kazuo Takechi; Yahiro Uemura, both of Osaka, all of Japan

[73] Assignee: Green Cross Corporation, Osaka, Japan

[21] Appl. No.: 71,685

[22] Filed: Jul. 9, 1987

[30] Foreign Application Priority Data

Jul. 9, 1986 [JP] Japan .................................. 61-161589
Aug. 30, 1986 [JP] Japan .................................. 61-204760

[51] Int. Cl.$^4$ .......................................... A61K 39/395
[52] U.S. Cl. .................................... 530/387; 424/85.8; 424/101; 514/8; 530/830
[58] Field of Search .................... 530/387, 830; 514/8, 514/21; 424/85, 101

[56] References Cited

U.S. PATENT DOCUMENTS

| | | | |
|---|---|---|---|
| 4,297,344 | 10/1981 | Schwinn | 424/101 |
| 4,374,763 | 2/1983 | Takagi | 530/387 |
| 4,396,608 | 8/1983 | Tenold | 424/85 X |
| 4,412,990 | 11/1983 | Lundblad et al. | 424/101 X |
| 4,424,206 | 1/1984 | Ohmura et al. | 424/101 |
| 4,439,421 | 3/1984 | Hooper et al. | 424/85 |
| 4,440,679 | 4/1984 | Fernandes et al. | 530/381 X |
| 4,477,432 | 10/1984 | Hardie | 424/85 |
| 4,478,829 | 10/1984 | Landaburu et al. | 514/21 |
| 4,579,735 | 4/1986 | Heimburger et al. | 424/101 |
| 4,623,717 | 11/1986 | Fernandes et al. | 530/386 X |
| 4,721,777 | 1/1988 | Uemura et al. | 530/387 X |

OTHER PUBLICATIONS

The Lancet, Nov., 1983, 1198–1199, Welch et al.

*Primary Examiner*—Howard E. Schain
*Attorney, Agent, or Firm*—Sughrue, Mion, Zinn, Macpeak & Seas

[57] ABSTRACT

A process for heat treating an aqueous solution containing chemically unmodified γ-globulin, wherein said heat treating is carried out in the presence of sorbitol is disclosed. By the heat treatment, impurity viruses can be inactivated without causing impairment of activities of chemically unmodified γ-globulin, increasing polymer contents or increasing an anticomplement titer.

6 Claims, No Drawings

PROCESS FOR HEAT TREATING CHEMICALLY UNMODIFIED GAMMA-GLOBULIN

FIELD OF THE INVENTION

This invention relates to a process for heat treating an aqueous solution containing chemically unmodified γ-globulin. More particularly, it relates to a process for heat treating chemically unmodified γ-globulin in the presence of a specific stabilizer without causing an increase of polymer contents or an increase of an anticomplement titer or impairing activities of the chemically unmodified γ-globulin.

BACKGROUND OF THE INVENTION

Of chemically unmodified immune globulins that are plasmaprotein components, chemically unmodified γ-gobulin preparations mainly comprising IgG have been widely utilized for prevention and treatment of various infectious diseases. The chemically unmodified γ-globulin has not been subjected to heat sterilization because of lack in heat stability and inclusion of a large number of antibodies to various viruses and bacteria.

However, in obtaining chemically unmodified γ-globulin from a plasmaprotein fraction, it cannot be denied that impurity viruses, such as a hepatitic virus, may be incorporated into the preparations. Therefore, heat sterilization of the preparations has a great significance from the standpoint of inactivation of the impurity viruses.

The problem is that chemically unmodified γ-globulin, when heated in an ordinary aqueous solution, e.g., physiological saline, becomes white turbid in a short time, resulting in substantial deactivation due to denaturation of protein.

SUMMARY OF THE INVENTION

As a result of extensive investigations, it has now been found that when an aqueous solution containing chemically unmodified γ-globulin is heated for inactivation of impurity viruses, e.g., a hepatitic virus and an AIDS virus, addition of sorbitol to the solution markedly improves heat stability of the chemically unmodified γ-globulin. The present invention has been completed based on this finding.

The present invention relates to a process for heat treating an aqueous solution containing chemically unmodified γ-globulin in the presence of sorbitol.

DETAILED DESCRIPTION OF THE INVENTION

The chemically unmodified γ-globulin to which the present invention is applied is characterized in that: (1) it remains intact without receiving any modification or change so that it does not contain fragments of γ-globulin, e.g., Fab, F(ab')$_2$, Fc, etc.; (2) it does not suffer from reduction in complement titer or antibody spectrum; and (3) its anticomplementary activity (inhibitory activity on complement) is considerably lower than 20 units (CH 50 value) that is a level regarded safe based on Japan Biological Product Standard according to Notification No. 159 (October 1985) issued by Ministry of Public Welfare of Japan.

Chemically unmodified γ-globulin prepared by any process can be used in the present invention as long as it has a natural state and a low anticomplement titer. The most efficient process for obtaining such chemically unmodified γ-globulin comprises subjecting γ-globulin for intramuscular injection, which can be prepared by the use of currently employed equipments and is already used for medical purpose, to acid treatment to separate agglomerates therefrom. Where complexity of processings or yield is no consideration, γ-globulin agglomerates which causes anticomplementary activity are preferably removed by using noninic surface active agents to obtain γ-globulin having a low anticomplement titer.

The process of the present invention is applicable to any aqueous solution containing chemically unmodified γ-globulin with its degree of purification unlimited. In particular, a partially purified or highly purified aqueous solution is advantageously used. The content of the protein (chemically unmodified γ-globulin) in the aqueous solution to be heat treated is not particularly restricted, but preferably ranges from 0.1 to 30 w/v%. The aqueous solution generally has a pH of from 4.5 to 6.5, and is preferably adjusted with an appropriate buffer solution such as a phosphate buffer solution, a citrate buffer solution, an acetate buffer solution, etc. to have a pH between 5 and 6.

The amount of sorbitol to be added as a stabilizer usually ranges from 10 to 70 g, preferably from 30 to 70 g, and more preferably from 40 to 60 g, per 100 ml of the chemically unmodified γ-globulin aqueous solution.

It is preferable that the chemically unmodified γ-globulin aqueous solution to be heated has a low ionic strength, more preferably an ionic strength of not higher than 0.01, and most preferably not higher than 0.001.

The heat treatment according to the present invention can be carried out under conditions sufficient to inactivate impurity viruses. More specifically, it is carried out at a temperature of from 50° to 70° C., and preferably about 60° C., and a period of from 10 minutes to 20 hours, and preferably about 10 hours.

In order to demonstrate the effects of the present invention, experiments were conducted on effects of heat treatment with or without the stabilizer of the invention upon infectivity of various viruses which are liable to be present in preparations of chemically unmodified γ-globulin. In the experiments, a chemically unmodified γ-globulin sample to which each of variola virus, mumps virus, measles virus, vesicular stomatitis virus, chikungnya virus, polio virus, coxsackie virus and echovirus had been added was heated at 60° C. for 10 hours in the presence or absence of the stabilizer, and the viral infectivity was assayed with time. As a result, it was revealed that the viruses completely lose their infectivity by 10-hour heat treatment irrespective of whether the stabilizer is present or not. These results suggest that the heat treatment according to the present invention would inactive viruses other than those tested and that the viral infectivity can be sufficiently reduced by heat treatment of several minutes.

The test samples having received the heat treatment were examined for appearance, properties, polymer content, anticomplement titer, measles antibody titer, and acute toxicity. The results obtained proved that chemically unmodified γ-globulin preparations having been treated by the process of the present invention are highly safe and effective for medical use.

The preparations obtained by the process of this invention are usually in the form of a solution. In the case where a crude material is employed, the thus treated solution is purified in a usual manner and, if desired, may be subjected to dialysis or filtration to remove bacteria. The purified solution is then poured into vials so that each vial contains from 500 to 10,000 mg of chemically unmodified γ-globulin. The preparations are preserved under ambient conditions, and preferably at temperatures below 30° C. If desired, the preparations may be freeze-dried.

The heat-treated chemically unmodified γ-globulin preparations can be administered as such or after an appropriate known treatment, such as dilution with or dissolving in injectable distilled water. The dose level of chemically unmodified γ-globulin usually ranges from 2,500 to 5,000 mg/dose for adults or from 100 to 150 mg/Kg-body weight/dose for children.

The chemically unmodified γ-globulin preparations having been heat-treated according to the present invention have impurity viruses contained therein, e.g., hepatitic virus, an AIDS virus, etc., substantially inactivated while retaining high activities of the chemically unmodified γ-globulin. Therefore, these preparations are sufficiently freed from a possibility of infection with viruses.

In addition, the heat-treated chemically unmodified γ-globulin according to the present invention is excellent in water solubility so that the aqueous solution thereof maintains satisfactory solution stability. Further, the heat treatment of the present invention is effective to inhibit formation of polymeric substances and to suppress an increase in anticomplement titer. Thus, the heat treatment according to the present invention is very suitable for preparing injectable solutions for intravenous administration.

The present invention will now be illustrated in greater detail by way of the following Examples and Test Examples. Testing in these examples was conducted according to the following methods.

(1) Appearance:
Turbidity was evaluated through absorbance (optical density) at 60 nm.

(2) Polymer Content:
Determined by high performance liquid chromatography.

(3) Anticomplement Titer:
An anticomplement titer was measured in accordance with the method described in Capat and Mayer, *Experimental Immunochemistry*, 225 (1961) or Nishioka and Okada, *Men-eki no Seikagaku*, 103, Kyoritsu Shuppan (1971). That is, a sample was added to 100 U of a complement, and the decreased unit of the complement was determined, which was taken as an anticomplement titer.

(4) Measles Antibody Titer:
Determined in accordance with a test method of hemagglutination inhibition and expressed in international unit (IU/150 mg).

EXAMPLE 1

To 1 Kg of a Cohn fraction II+III was added 10 l of a 0.001M sodium chloride aqueous solution. After the solution was adjusted to a pH of 5.0, PEG #4000 was added thereto to a final concentration of 8 w/v%. The resulting mixture was subjected to centrifugation at 2° C.

The supernatant liquor was adjusted to a pH of 8.0 with 1N sodium hydroxide aqueous solution, and PEG #4000 was added thereto to a final concentration of 12 w/v%, followed by centrifugation at 2° C. to collect an IgG fraction.

The IgG fraction was dissolved in water to an IgG concentration of 7 w/v%, and the aqueous solution was adjusted to a pH of 6.5. The resulting aqueous solution was brought into contact with DEAE-Sephadex at a rate of 50 ml/ml of DEAE-Spehadex at a temperature of from 0° to 4° C. for about 1 hour, followed by centrifugation to recover a supernatant.

A 100 ml portion of the resulting supernatant liquor containing IgG was passed through a column packed with 5 ml of Benzamidine Sephalose (produced by Pharmacia Co.) and a column packed with 3 ml of Formyl Cellulofine ®, (Seikagaku Kogyo Co., Ltd.) a human blood group substance, to thereby remove a human blood group antibody by adsorption. The blood group antibody was decreased from (1:32) to (1:2) through the adsorption.

The effluent (non-adsorbed fraction) containing chemically unmodified γ-globulin was adjusted to have a concentration of 5 w/v%, and sorbitol as a stabilizer was added thereto to a concentration of 20 w/v% (20 g of sorbitol per 100 ml of the γ-globulin solution). The solution was then subjected to heat treatment at 60° C. for one hour, with its ionic strength and pH value being varied as shown in Table 1.

For comparison, samples were prepared in the same manner as described above, except for adding no stabilizer or conducting no heat treatment. Each of the thus prepared samples was evaluated by the above-described methods, and the results obtained are shown in Table 1.

It can be seen from the Table that heat stability of chemically unmodified γ-globulin can be improved by heat treatment in the presence of sorbitol and that the effect on heat stability improvement can be ensured by adjusting the chemically unmodified γ-globulin aqueous solution to have an ionic strength of from 0 to 0.01, and particularly 0.001 or less, and a pH value of from 4.5 to 6.5, and particularly from 5 to 6.

TABLE 1

| Ionic Strength | Sorbitol Concentration (w/v %) | Heat Treatment | pH | Optical Density (600 nm) | Polymer Content (wt %) | | | Anticomplement Titer |
|---|---|---|---|---|---|---|---|---|
| | | | | | Polymer | Dimer | Monomer | |
| <0.001 | 20 | 60° C., 1 Hr. | 4.0 | 0.010 | 0.98 | 12.74 | 86.26 | — |
| " | " | " | 5.0 | 0.011 | 0.09 | 2.31 | 97.13 | 8 |
| " | " | " | 6.0 | 0.010 | 0.06 | 3.95 | 95.63 | 12 |
| " | " | " | 7.0 | Slight Turbidity | — | — | — | 64 |
| " | Not Added | " | 5.0 | White Turbidity | — | — | — | — |
| " | " | Undone | 5.0 | 0.010 | 0 | 9.09 | 90.86 | 8 |
| 0.080 | 20 | 60° C., 1 Hr. | 4.0 | Slight Turbidity | — | — | — | — |

TABLE 1-continued

| Ionic Strength | Sorbitol Concentration (w/v %) | Heat Treatment | pH | Optical Density (600 nm) | Polymer Content (wt %) Polymer | Dimer | Monomer | Anticomplement Titer |
|---|---|---|---|---|---|---|---|---|
| " | " | " | 5.0 | Slight Turbidity | — | — | — | — |
| " | " | " | 6.0 | White Turbidity | — | — | — | — |
| " | " | " | 7.0 | White Turbidity | — | — | — | — |
| " | Not Added | " | 5.0 | White Turbidity | — | — | — | — |
| " | " | Undone | 5.0 | 0.011 | 0 | 9.14 | 90.84 | 9 |
| 0.160 | 20 | 60° C., 1 Hr. | 4.0 | Slight Turbidity | — | — | — | — |
| " | " | " | 5.0 | Slight Turbidity | — | — | — | — |
| " | " | " | 6.0 | White Turbidity | — | — | — | — |
| " | " | " | 7.0 | White Turbidity | — | — | — | — |
| " | Not Added | " | 5.0 | White Turbidity | — | — | — | — |
| " | " | Undone | 5.0 | 0.014 | 0 | 9.15 | 90.82 | 8 |

EXAMPLE 2

To the chemically unmodified γ-globulin solution as prepared in Example 1 (chemically unmodified γ-globulin concentration: 5 w/v%) was added sorbitol in an amount shown in Table 2. The resulting solution was heated at 60° C. for a period shown in the Table. Each of the samples thus obtained was evaluated in accordance with the abovedescribed test methods, and the results obtained are shown in the Table.

As is apparent from Table 2, systems containing 10 g/dl of sorbitol show white turbidity within one hour after the heat treatment and undergo denaturation, formation of polymers, and increase in anticomplement titer while depending on the pH value of the system. On the other hand, the systems containing 15 g/dl of sorbitol exhibit improved heat stability.

| Amount of Sorbitol* (g/dl) | pH | Heating Time (60° C.) (hr) | Polymer Content (wt %) Polymer | Dimer | Monomer | Anticomplement Titer | Antibody Titer (IU) |
|---|---|---|---|---|---|---|---|
| Not Added | — | Undone | — | 9.09 | 90.56 | 8 | 42 |
| 10 | 4.0 | 1 | 1.39 | 10.25 | 81.78 | 25 | — |
| " | 5.0 | " | 1.21 | 2.82 | 95.46 | 25 | — |
| " | 6.0 | " | 2.65 | 4.39 | 92.46 | 27 | — |
| " | 7.0 | " | Slight Turbidity | Slight Turbidity | Slight Turbidity | — | — |
| 15 | 4.6 | " | 0.55 | 0.84 | 98.12 | 24 | — |
| " | 4.8 | " | 0.40 | 0.98 | 98.14 | 14 | 42 |
| " | 5.0 | " | 0.51 | 0.79 | 98.65 | 16 | 42 |
| " | 5.2 | " | 0.41 | 1.48 | 97.69 | 17 | 42 |
| " | 5.4 | " | 0.40 | 1.86 | 97.32 | 14 | 42 |
| 20 | 4.0 | " | 0.98 | 12.74 | 86.26 | — | — |
| " | 5.0 | " | 0.09 | 2.31 | 97.13 | 8 | 42 |
| " | 6.0 | " | 0.06 | 3.95 | 95.63 | 12 | 42 |
| 20 | 7.0 | 1 | Slight Turbidity | Slight Turbidity | Slight Turbidity | 64 | — |
| " | 5.0 | 3 | 0.35 | 3.18 | 96.45 | — | — |
| " | 6.0 | " | 1.76 | 7.53 | 90.58 | — | — |
| " | 7.0 | " | 3.57 | 8.33 | 88.09 | — | — |
| 30 | 5.0 | 10 | 3.15 | 3.63 | 93.15 | 9 | 42 |
| " | 5.5 | " | 1.38 | 3.33 | 95.21 | 12 | 42 |
| " | 6.0 | " | 1.59 | 5.85 | 92.55 | 19 | 42 |
| 40 | 5.0 | " | 0.46 | 1.97 | 97.50 | 11 | 42 |
| " | 5.5 | " | 0.52 | 3.59 | 95.87 | 9 | 42 |
| " | 6.0 | " | 0.55 | 5.65 | 93.79 | 18 | 42 |
| 50 | 5.0 | " | 0.15 | 1.92 | 97.87 | 12 | 42 |
| " | 5.5 | " | 0.22 | 2.87 | 96.89 | 13 | 42 |
| " | 6.0 | " | 0.26 | 3.70 | 95.98 | 19 | 42 |

Note:
*gram per 100 ml of a γ-globulin aqueous solution

TEST EXAMPLE

Acute Toxicity

Each of samples having been heat treated at pH 5.0 in Example 1 was thoroughly dialyzed against sterilized physiological saline, and the dialyzate was administered to mice (5 mice per group) through the tail vein at a dose of 0.5 ml or 1.0 ml/animal. The animals were observed for 7 days, but no abnormality was noted. $LD_{50}$ of the samples was determined using mice and each sample exhibited $LD_{50}$ of 50 mg/mouse or more.

While the invention has been described in detail and with reference to specific embodiments thereof, it will be apparent to one skilled in the art that various changes and modifications can be made therein without departing from the spirit and scope thereof.

What is claimed is:

1. A process for heat treating an aqueous solution containing chemically unmodified γ-globulin, wherein said heat treating is carried out in the presence of a stabilizer consisting of sorbitol and said aqueous solution has an ionic strength of 0.001 or less and a pH of from 4.5 to 6.5.

2. A process as claimed in claim 1, wherein sorbitol is present in an amount of from 10 to 70 g per 100 ml of the aqueous solution.

3. A process as claimed in claim 2, wherein sorbitol is present in an amount of from 30 to 70 g per 100 ml of the aqueous solution.

4. A process as claimed in claim 3, wherein sorbitol is present in an amount of from 40 to 60 g per 100 ml of the aqueous solution.

5. A process as claimed in claim 1, wherein said heat treating is carried out at a temperature of from 50° to 70° C. for a period of from 10 minutes to 20 hours.

6. A process for heat treating an aqueous solution containing chemically unmodified γ-globulin, wherein said heat treating is carried out in the presence of a stabilizer consisting of sorbitol and said aqueous solution has an ionic strength of 0.001 or less and a pH of from 5 to 6.

* * * * *